United States Patent
Clozel et al.

(10) Patent No.: US 11,672,783 B2
(45) Date of Patent: *Jun. 13, 2023

(54) PHARMACEUTICAL COMBINATION COMPRISING A SELECTIVE S1P1 RECEPTOR AGONIST

(71) Applicant: ACTELION PHARMACEUTICALS LTD, Allschwil (CH)

(72) Inventors: Martine Clozel, Allschwil (CH); Luca Piali, Basel (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 202 days.

This patent is subject to a terminal disclaimer.

(21) Appl. No.: 17/325,912

(22) Filed: May 20, 2021

(65) Prior Publication Data

US 2021/0338640 A1 Nov. 4, 2021

Related U.S. Application Data

(60) Continuation of application No. 16/277,829, filed on Feb. 15, 2019, now Pat. No. 11,026,927, which is a division of application No. 15/534,951, filed as application No. PCT/EP2015/079311 on Dec. 10, 2015, now Pat. No. 10,245,253.

(30) Foreign Application Priority Data

Dec. 11, 2014 (WO) .................. PCT/EP2014/077469

(51) Int. Cl.
| | | |
|---|---|---|
| *A61K 31/426* | (2006.01) | |
| *A61K 31/22* | (2006.01) | |
| *A61K 31/225* | (2006.01) | |
| *A61K 31/4015* | (2006.01) | |
| *A61K 9/00* | (2006.01) | |
| *A61K 31/27* | (2006.01) | |

(52) U.S. Cl.
CPC .......... *A61K 31/426* (2013.01); *A61K 9/0053* (2013.01); *A61K 31/22* (2013.01); *A61K 31/225* (2013.01); *A61K 31/27* (2013.01); *A61K 31/4015* (2013.01)

(58) Field of Classification Search
CPC .............................. A61K 31/426; A61K 31/22
See application file for complete search history.

(56) References Cited

U.S. PATENT DOCUMENTS

| | | |
|---|---|---|
| 4,959,389 A | 9/1990 | Speiser et al. |
| 7,435,828 B2 | 10/2008 | Binkert et al. |
| 7,626,037 B2 | 12/2009 | Binkert et al. |
| 7,875,726 B2 | 1/2011 | Binkert et al. |
| 8,263,780 B2 | 9/2012 | Abele et al. |
| 8,273,779 B2 | 9/2012 | Binkert et al. |
| RE43,728 E | 10/2012 | Binkert et al. |
| RE43,833 E | 11/2012 | Binkert et al. |
| 8,399,514 B2 | 3/2013 | Lukashev et al. |
| 8,524,752 B2 | 9/2013 | Binkert et al. |
| 8,669,281 B1 | 3/2014 | Zeidan et al. |
| 8,785,484 B2 | 7/2014 | Brossard et al. |
| RE45,174 E | 9/2014 | Binkert et al. |
| 8,912,340 B2 | 12/2014 | Abele et al. |
| 9,000,018 B2 | 4/2015 | Binkert et al. |
| 9,062,014 B2 | 6/2015 | Bonham et al. |
| 9,340,518 B2 | 5/2016 | Herse et al. |
| 10,220,023 B2 | 3/2019 | Dingemanse et al. |
| 10,245,253 B2* | 4/2019 | Clozel .................. A61P 43/00 |
| 11,026,927 B2* | 6/2021 | Clozel .................. A61P 25/00 |
| 2010/0260755 A1 | 10/2010 | Gammans et al. |
| 2013/0314669 A1 | 11/2013 | Levin et al. |
| 2014/0303217 A1 | 10/2014 | Brossard et al. |
| 2014/0315964 A1 | 10/2014 | Brossard et al. |
| 2014/0316140 A1 | 10/2014 | Brossard et al. |
| 2015/0203493 A1 | 6/2015 | Gucklan et al. |
| 2015/0183741 A1 | 7/2015 | Gucklan et al. |
| 2015/0265580 A1 | 9/2015 | Brossard et al. |

FOREIGN PATENT DOCUMENTS

| | | |
|---|---|---|
| AU | 752733 | 9/2002 |
| AU | 2013329421 | 4/2014 |
| DE | 102009008851 | 8/2010 |
| DE | 102010048788 | 5/2011 |
| DE | 102010026879 | 8/2011 |
| EP | 0 312 697 | 4/1989 |
| EP | 2 137 537 | 8/2008 |

(Continued)

OTHER PUBLICATIONS

"Abstracts—ACTRIMS Forum 2017," Multiple Sclerosis Journal, vol. 23, p. 2-90, (2017).

(Continued)

*Primary Examiner* — Svetlana M Ivanova

(74) *Attorney, Agent, or Firm* — BakerHostetler

(57) ABSTRACT

The present invention relates to a pharmaceutical combination comprising a first active ingredient which is (R)-5-[3-chloro-4-(2,3-dihydroxy-propoxy)-benz[Z]ylidene]-2-([Z] propylimino)-3-o-tolyl-thiazolidin-4-one or a pharmaceutically acceptable salt thereof and a second active ingredient which is selected from the group consisting of methyl fumarate, dimethyl fumarate, (N,N-diethylcarbamoyl)methyl methyl (2E)but-2-ene-1,4-dioate, and 2-(2,5-dioxopyrrolidin-1-yl)ethyl methyl (2E)but-2-ene-1,4-dioate, or a pharmaceutically acceptable salt thereof.

15 Claims, 1 Drawing Sheet

(56) References Cited

FOREIGN PATENT DOCUMENTS

| | | |
|---|---|---|
| EP | 2 177 521 | 4/2010 |
| EP | 2 202 232 | 6/2010 |
| EP | 2 210 890 | 7/2010 |
| EP | 2 305 660 | 4/2011 |
| EP | 2 316 430 | 5/2011 |
| EP | 2 343 287 | 7/2011 |
| EP | 2 366 702 | 9/2011 |
| EP | 2 390 252 | 11/2011 |
| EP | 2 455 080 | 5/2012 |
| EP | 2 692 344 | 2/2014 |
| JP | T-2012-500285 | 1/2012 |
| WO | WO 00/030622 | 6/2000 |
| WO | WO 2005/054215 | 6/2005 |
| WO | WO 2008/062376 | 5/2008 |
| WO | WO 2008/097596 | 8/2008 |
| WO | WO 2009/115954 | 9/2009 |
| WO | WO 2010/022177 | 2/2010 |
| WO | WO 2010/046835 | 4/2010 |
| WO | WO 2010/079222 | 7/2010 |
| WO | WO 2011/067243 | 6/2011 |
| WO | WO 2012/162669 | 11/2012 |
| WO | WO 2012/164026 | 12/2012 |
| WO | WO 2013/119677 A1 | 8/2013 |
| WO | WO 2013/148690 | 10/2013 |
| WO | WO 2014/018891 | 1/2014 |
| WO | WO 2014/020156 | 2/2014 |
| WO | WO 2014/027330 | 2/2014 |
| WO | WO 2014/028299 | 2/2014 |
| WO | WO 2014/031844 | 2/2014 |
| WO | WO 2014/031892 | 2/2014 |
| WO | WO 2014/058875 | 4/2014 |
| WO | WO 2014/071371 | 5/2014 |
| WO | WO 2014/152494 | 9/2014 |
| WO | WO 2015/066515 | 5/2015 |
| WO | WO 2016/091996 | 6/2016 |

OTHER PUBLICATIONS

Brennan et al., "Dimethyl Fumarate and Monomethyl Fumarate are Distinguished by Non-Overlapping Pharmacodynamic Effects In Vivo (P1.206)," Neurology, vol. 82(10 Supplement), 4 pages, (2014); Abstract Only.

Brossard et al., "Pharmacokinetics and pharmacodynamics of ponesimod, a selective $S1P_1$ receptor modulator, in the first-in-human study," British Journal of Clinical Pharmacology, vol. 76(6), p. 888-896, (2013).

Cohen et al., "The future of multiple sclerosis treatment," Journal of the Neurological Sciences, vol. 277, S1, p. S55-S61, (2009).

Curtin et al., "Novel Therapeutic Options for Multiple Sclerosis", Expert Rev. Clin. Pharmacol., vol. 7(1), p. 91-104, (2014).

Ellwardt et al., "Molecular Mechanisms Linking Neuroinflammation and Neurodegeneration in MS," Experimental Neurology, vol. 262, p. 8-17, (2014).

Fernandez et al., "Review of the novelties presented at the 28th Congress of the European Committee for Treatment and Research in Multiple Sclerosis (ECTRIMS) (III)," Rev. Neurol., vol. 57(7), p. 317-329, (2013).

Fernandez et al., "Combination therapy in multiple sclerosis," Journal of the Neurological Sciences, vol. 259, p. 95-103, (2007).

International Search Report of International Application No. PCT/EP2015/079311, dated Feb. 25, 2016, 7 pages.

Olsson et al., "Oral ponesimod in relapsing-remitting multiple sclerosis: a randomised phase II trial," Journal of Neurology, Neurosurgery and Psychiatry, vol. 85, p. 1198-1208, (2014).

Pitarokoili et al., "Lewis Rat Model of Experimental Autoimmune Encephalomyelitis," Current Protocols in Neuroscience, vol. 81, 22 pages, (2017).

Pouzol et al., "Complete resolution of clinical signs and synergism of the combination ponesimod-dimethyl fumarate in rat models of multiple sclerosis," Actelion Pharmaceuticals Ltd—Poster DMF-ponesimod ACTRIMS, (2017).

Remington, "The Science and Practice of Pharmacy," 21st Ed., Part 5, Pharmaceutical Manufacturing, p. 689-1058, (2005).

Shin et al., "Mechanisms of Experimental Autoimmune Encephalomyelitis in Lewis Rats: Recent Insights from Macrophages," Anat Cell Biol, vol. 45, p. 141-148, (2012).

Shurin et al. "Immune-mediated diseases: where do we stand?," Advances in Experimental Medicine and Biology, vol. 601, p. 1-12, (2007).

Stahl et al., Handbook of Pharmaceutical Salts, Properties, Selection and Use, p. 330-350, (2008).

Weaver et al., "An elevated matrix metalloproteinase (MMP) in an animal model of multiple sclerosis is protective by affecting Th1/Th2 polarization," The FASEB Journal, vol. 19(12), p. 1668-1670, (2005).

Wouters et al., "Pharmaceutical Salts and Co-crystals", RSC Publishing, (2012).

Wustrow et al., "Comparison of the Efficacy and Tolerability of a Novel Methyl Hydrogenfumarate Prodrug with Dimethyl Fumarate in Rodent EAE and GI Irritation Models," Neurology, vol. 76(9), Suppl. 4, p. A387, (2011), XP008164466.

* cited by examiner

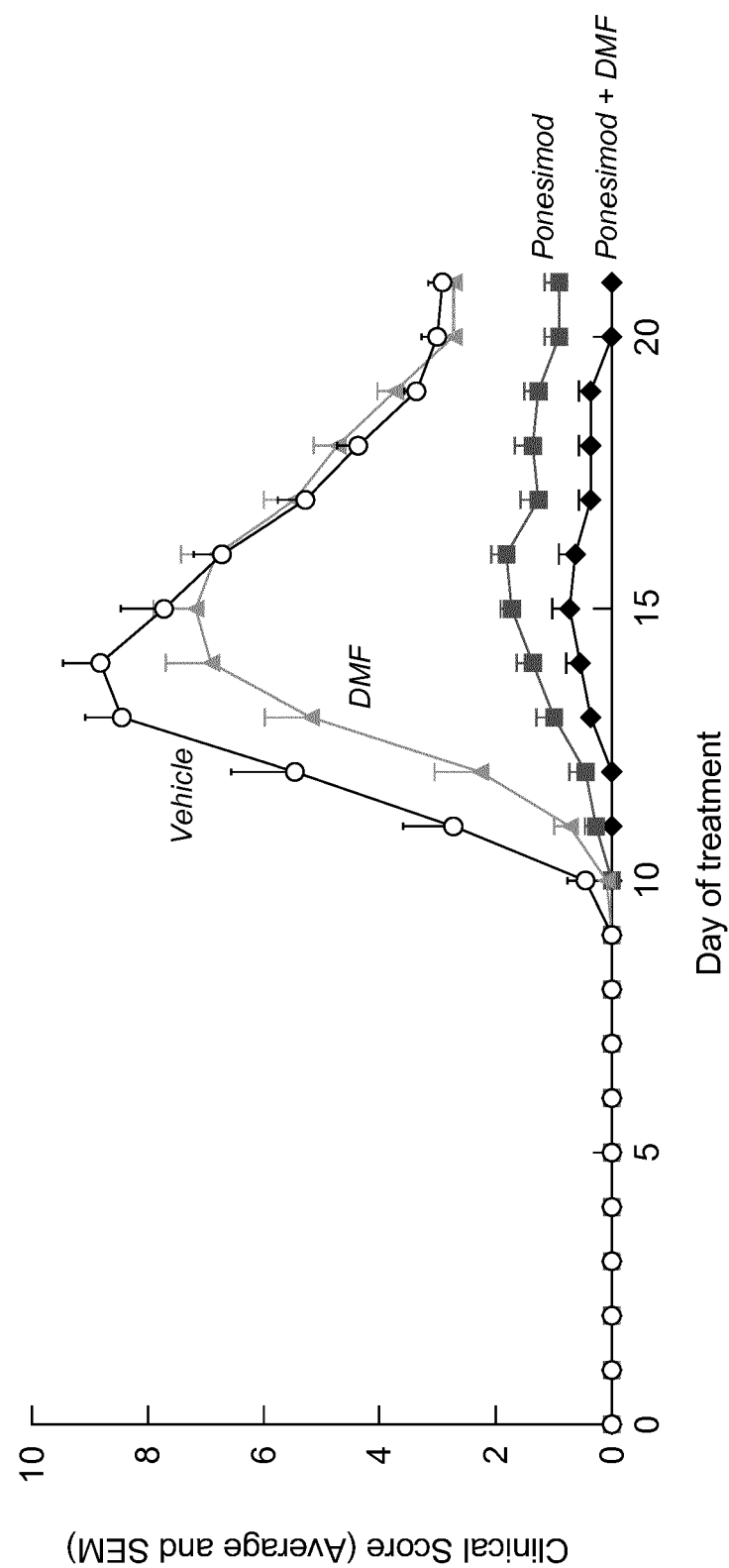

PHARMACEUTICAL COMBINATION COMPRISING A SELECTIVE S1P1 RECEPTOR AGONIST

CROSS REFERENCE TO RELATED APPLICATIONS

This application is a continuation application of U.S. patent application Ser. No. 16/277,829, filed Feb. 15, 2019, which is a divisional application of U.S. application Ser. No. 15/534,951, filed on Jun. 9, 2017, which claims the benefit of United States Application under 35 U.S.C. 371 claiming benefit of PCT Application No. PCT/EP2015/079311, filed on Dec. 10, 2015, which claims the benefit of PCT Application No. PCT/EP2014/077469, filed on Dec. 11, 2014, the contents of each of which are incorporated herein by reference.

The present invention relates to a pharmaceutical combination comprising a first active ingredient which is (R)-5-[3-chloro-4-(2,3-dihydroxy-propoxy)-benz[Z]ylidene]-2-([Z]-propylimino)-3-o-tolyl-thiazolidin-4-one or a pharmaceutically acceptable salt thereof and a second active ingredient which is selected from the group consisting of methyl fumarate, dimethyl fumarate, (N,N-diethylcarbamoyl)methyl methyl (2E)but-2-ene-1,4-dioate, and 2-(2,5-dioxopyrrolidin-1-yl)ethyl methyl (2E)but-2-ene-1,4-dioate, or a pharmaceutically acceptable salt thereof.

DESCRIPTION OF THE FIGURE

FIG. 1: Efficacy of ponesimod, DMF or its combination in rat EAE (n=11/group). Clinical scoring was performed daily by an independent examiner in a blinded manner. SEM=standard error of the mean.

DESCRIPTION OF THE INVENTION

1) In a first embodiment the present invention relates to a pharmaceutical combination comprising a first active ingredient which is (R)-5-[3-chloro-4-(2,3-dihydroxy-propoxy)-benz[Z]ylidene]-2-([Z]-propylimino)-3-o-tolyl-thiazolidin-4-one (hereinafter also referred to as "COMPOUND 1") or a pharmaceutically acceptable salt thereof and a second active ingredient which is selected from the group consisting of methyl fumarate, dimethyl fumarate, (N,N-diethylcarbamoyl)methyl methyl (2E)but-2-ene-1,4-dioate, and 2-(2,5-dioxopyrrolidin-1-yl)ethyl methyl (2E)but-2-ene-1,4-dioate, or a pharmaceutically acceptable salt thereof.

WO 2010/046835 discloses different crystalline forms of COMPOUND 1; it is to be understood that the present invention encompasses COMPOUND 1 in any form including amorphous as well as crystalline forms of COMPOUND 1. It is further to be understood that crystalline forms of COMPOUND 1 encompasses all types of crystalline forms of COMPOUND 1 including polymorphs of the mere molecule, solvates and hydrates, molecular salts and co-crystals (when the same molecule can be co-crystallized with different co-crystal formers) provided they are suitable for pharmaceutical administration. In a preferred embodiment, COMPOUND 1 is in crystalline form A or C as described in WO 2010/046835. In a most preferred embodiment, COMPOUND 1 is in crystalline form C.

Likewise it is to be understood that the present invention encompasses methyl fumarate, dimethyl fumarate, (N,N-diethylcarbamoyl)methyl methyl (2E)but-2-ene-1,4-dioate, and 2-(2,5-dioxopyrrolidin-1-yl)ethyl methyl (2E)but-2-ene-1,4-dioate in any form including amorphous as well as crystalline forms as described for COMPOUND 1 in the preceding paragraph. The term "methyl fumarate" as used herein refers to (E)-4-methoxy-4-oxobut-2-enoic acid and/or pharmaceutically acceptable salts thereof.

COMPOUND 1 is a selective $S1P_1$ receptor agonist and oral administration thereof results in a consistent, sustained, and dose-dependent reduction in the number of peripheral blood lymphocytes. COMPOUND 1 has been described to be useful in the treatment and/or prevention of diseases or disorders associated with an activated immune system (see e.g. WO 2005/054215 and WO 2009/115954). In particular COMPOUND 1 (INN: ponesimod) has shown clinical benefit in phase II trials in patients with moderate to severe chronic plaque psoriasis and in patients with relapsing-remitting multiple sclerosis. COMPOUND 1 may be prepared according to any procedure as disclosed in WO 2005/054215, WO 2008/062376 and WO 2014/027330.

Dimethyl fumarate (also termed "DMF" of "BG-12") has been described in WO 00/030622 to be useful for the treatment of autoimmune diseases. In particular dimethyl fumarate (Tecfidera®) has been approved for the treatment of relapsing forms of multiple sclerosis, including relapsing-remitting multiple sclerosis, which is the most common form of the disease. Dimethyl fumarate can be prepared according to procedures known in the art for example as described in EP 0312697 A2.

Methyl fumarate (also termed "monomethyl fumarate" or "MMF") has been shown to be a pharmacologically active metabolite of dimethyl fumarate. Methyl fumarate can be prepared according to procedures known in the art for example as described in EP 0312697 A2.

(N,N-Diethylcarbamoyl)methyl methyl (2E)but-2-ene-1,4-dioate (also termed "XP23829") is a prodrug that is rapidly converted to monomethyl fumarate. XP23829 is currently in clinical development for the treatment of moderate-to-severe chronic plaque-type psoriasis and for the treatment of relapsing forms of multiple sclerosis. (N,N-diethylcarbamoyl)methyl methyl (2E)but-2-ene-1,4-dioate and the preparation thereof is described in WO 2010/022177.

2-(2,5-Dioxopyrrolidin-1-yl)ethyl methyl (2E)but-2-ene-1,4-dioate (also termed "ALKS 8700") is a prodrug that rapidly converts to monomethyl fumarate. ALKS 8700 is currently in clinical development for the treatment of multiple sclerosis. 2-(2,5-Dioxopyrrolidin-1-yl)ethyl methyl (2E)but-2-ene-1,4-dioate and the preparation thereof is described in WO 2014/152494.

2) A further embodiment of the invention relates to a pharmaceutical combination according to embodiment 1), wherein the first active ingredient is (R)-5-[3-chloro-4-(2,3-dihydroxy-propoxy)-benz[Z]ylidene]-2-([Z]-propylimino)-3-o-tolyl-thiazolidin-4-one and the second active ingredient is methyl fumarate or a pharmaceutically acceptable salt thereof.

3) A further embodiment of the invention relates to a pharmaceutical combination according to embodiment 1), wherein the first active ingredient is (R)-5-[3-chloro-4-(2,3-dihydroxy-propoxy)-benz[Z]ylidene]-2-([Z]-propylimino)-3-o-tolyl-thiazolidin-4-one and the second active ingredient is dimethyl fumarate.

4) A further embodiment of the invention relates to a pharmaceutical combination according to embodiment 1), wherein the first active ingredient is (R)-5-[3-chloro-4-(2,3-dihydroxy-propoxy)-benz[Z]ylidene]-2-([Z]-propylimino)-3-o-tolyl-thiazolidin-4-one and the second active ingredient is (N,N-diethylcarbamoyl)methyl methyl (2E)but-2-ene-1,4-dioate.

5) A further embodiment of the invention relates to a pharmaceutical combination according to embodiment 1), wherein the first active ingredient is (R)-5-[3-chloro-4-(2,3-dihydroxy-propoxy)-benz[Z]ylidene]-2-([Z]-propylimino)-3-o-tolyl-thiazolidin-4-one and the second active ingredient is 2-(2,5-dioxopyrrolidin-1-yl)ethyl methyl (2E)but-2-ene-1,4-dioate.

6) A further embodiment of the invention relates to a pharmaceutical combination according to any one of embodiments 1) to 5), wherein the first and the second active ingredient are comprised in a single pharmaceutical composition.

In a special case of embodiment 6) where e.g. the first active ingredient is administered once daily and the second ingredient is administered twice daily, only one of the two pharmaceutical compositions needed per day will contain both the first and the second active ingredient whereas the other will only contain the second active ingredient.

Moreover, in case of a pharmaceutical combination according to embodiment 6) where the first and/or the second active ingredient is admistered according to a dose up-titration regimen (see for example the up-titration regimen disclosed in WO 2009/115954 for COMPOUND 1) the pharmaceutical compositions needed for the dose up-titration will contain the amounts of active ingredient required for the different steps of the dose up-titration regimen.

7) A further embodiment of the invention relates to a pharmaceutical combination according to any one of embodiments 1) to 5), wherein the first and the second active ingredient are comprised in separated pharmaceutical compositions.

In case the first and the second active ingredient are comprised in separated pharmaceutical compositions, they can be administered simultaneously, sequentially or separately; preferably the separated pharmaceutical compositions are administered simultaneously or sequentially, especially sequentially. In case the first active ingredient is for example administered once daily and the second active ingredient twice daily, then the separated pharmaceutical compositions are preferably administered one time per day simultaneously or sequentially, especially sequentially. If administered sequentially or separately, the separated pharmaceutical compositions may be administered in one or the other order. The number of administrations per day may be the same or different for the separated pharmaceutical compositions. For instance, one pharmaceutical composition may be administered twice daily and the other pharmaceutical composition may be administered once or twice daily. Preferably the pharmaceutical composition comprising COMPOUND 1 is administered once daily and the pharmaceutical composition comprising the second active ingredient is administered twice daily. Further, the separated pharmaceutical compositions may be administered by the same or different routes of administration, preferably by the same route of administration. Most preferably the separated pharmaceutical compositions are administered orally.

8) A further embodiment of the invention relates to a pharmaceutical combination according to any one of embodiments 1) to 7) for use as a medicament.

9) A further embodiment of the invention relates to a pharmaceutical combination according to any one of embodiments 1) to 7) for use in the prevention and/or treatment of a disease or disorder associated with an activated immune system.

10) A further embodiment of the invention relates to a pharmaceutical combination according to any one of embodiments 1) to 7) for use in the prevention and/or treatment of a disease or disorder selected from the group consisting of rejection of transplanted organs such as kidney, liver, heart, lung, pancreas, cornea, and skin; graft-versus-host disease; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and dermatitis; asthma; type I diabetes; post-infectious autoimmune diseases including rheumatic fever and post-infectious glomerulonephritis; solid cancers; and tumor metastasis.

11) A further embodiment of the invention relates to a pharmaceutical combination according to any one of embodiments 1) to 7) for use in the prevention and/or treatment of a disease or disorder selected from the group consisting of rejection of transplanted organs selected from kidney, liver, heart and lung; graft-versus-host disease; autoimmune syndromes selected from rheumatoid arthritis, multiple sclerosis, psoriasis, psoriatic arthritis, Crohn's disease, and Hashimoto's thyroiditis; and atopic dermatitis.

12) A preferred embodiment of the invention relates to a pharmaceutical combination according to any one of embodiments 1) to 7) for use in the prevention and/or treatment of graft-versus-host disease.

13) A most preferred embodiment of the invention relates to a pharmaceutical combination according to any one of embodiments 1) to 7) for use in the prevention and/or treatment of multiple sclerosis.

14) Another very preferred embodiment of the invention relates to a pharmaceutical combination according to any one of embodiments 1) to 7) for use in the prevention and/or treatment of relapsing multiple sclerosis.

15) Another very preferred embodiment of the invention relates to a pharmaceutical combination according to any one of embodiments 1) to 7) for use in the prevention and/or treatment of relapsing-remitting multiple sclerosis.

The present invention also relates to a method for the prevention or treatment of a disease or disorder listed in any one of embodiments 9) to 15) comprising administering to a subject (preferably a human subject) in need thereof a pharmaceutically active amount of a pharmaceutical combination according to any one of embodiments 1) to 7).

16) A further embodiment of the invention relates to a pharmaceutical composition containing, as active principle, (R)-5-[3-chloro-4-(2,3-dihydroxy-propoxy)-benz[Z]ylidene]-2-([Z]-propylimino)-3-o-tolyl-thiazolidin-4-one and at least one therapeutically inert excipient, wherein the pharmaceutical composition is to be administered in combination with a second pharmaceutical composition containing, as active principle, methyl fumarate, dimethyl fumarate, (N,N-diethylcarbamoyl)methyl methyl (2E)but-2-ene-1,4-dioate, or 2-(2,5-dioxopyrrolidin-1-yl)ethyl methyl (2E)but-2-ene-1,4-dioate, or a pharmaceutically acceptable salt thereof and at least one therapeutically inert excipient.

17) A further embodiment of the invention relates to a pharmaceutical composition containing, as active principle, (R)-5-[3-chloro-4-(2,3-dihydroxy-propoxy)-benz[Z]ylidene]-2-([Z]-propylimino)-3-o-tolyl-thiazolidin-4-one and at least one therapeutically inert excipient, wherein the pharmaceutical composition is to be administered in combination with a second pharmaceutical composition containing, as active principle, dimethyl fumarate and at least one therapeutically inert excipient.

18) A further embodiment of the invention relates to a pharmaceutical composition according to embodiment 16) or 17) for use as a medicament.

19) A further embodiment of the invention relates to a pharmaceutical composition according to embodiment 16) or 17) for use in the prevention and/or treatment of a disease or disorder listed in any one of embodiments 9) to 15).

20) A further embodiment of the invention relates to a pharmaceutical composition containing, as active principle, methyl fumarate, dimethyl fumarate, (N,N-diethylcarbamoyl)methyl methyl (2E)but-2-ene-1,4-dioate, or 2-(2,5-dioxopyrrolidin-1-yl)ethyl methyl (2E)but-2-ene-1,4-dioate, or a pharmaceutically acceptable salt thereof, and at least one therapeutically inert excipient, wherein the pharmaceutical composition is to be administered in combination with a second pharmaceutical composition containing, as active principle, (R)-5-[3-chloro-4-(2,3-dihydroxy-propoxy)-benz[Z]ylidene]-2-([Z]-propylimino)-3-o-tolyl-thiazolidin-4-one and at least one therapeutically inert excipient.

21) A further embodiment of the invention relates to a pharmaceutical composition containing, as active principle, dimethyl fumarate and at least one therapeutically inert excipient, wherein the pharmaceutical composition is to be administered in combination with a second pharmaceutical composition containing, as active principle, (R)-5-[3-chloro-4-(2,3-dihydroxy-propoxy)-benz[Z]ylidene]-2-([Z]-propylimino)-3-o-tolyl-thiazolidin-4-one and at least one therapeutically inert excipient.

22) A further embodiment of the invention relates to a pharmaceutical composition according to embodiment 20) or 21) for use as a medicament.

23) A further embodiment of the invention relates to a pharmaceutical composition according to embodiment 20) or 21) for use in the prevention and/or treatment of a disease or disorder listed in any one of embodiments 9) to 15).

24) A further embodiment of the invention relates to a kit of parts comprising a first pharmaceutical composition containing, as active principle, (R)-5-[3-chloro-4-(2,3-dihydroxy-propoxy)-benz[Z]ylidene]-2-([Z]-propylimino)-3-o-tolyl-thiazolidin-4-one and at least one therapeutically inert excipient; and a second pharmaceutical composition containing, as active principle, methyl fumarate, dimethyl fumarate, (N,N-diethylcarbamoyl)methyl methyl (2E)but-2-ene-1,4-dioate, or 2-(2,5-dioxopyrrolidin-1-yl)ethyl methyl (2E)but-2-ene-1,4-dioate, or a pharmaceutically acceptable salt thereof, and at least one therapeutically inert excipient.

25) A further embodiment of the invention relates to a kit of parts according to embodiment 24), wherein the second pharmaceutical composition contains, as active principle, dimethyl fumarate and at least one therapeutically inert excipient.

26) A further embodiment of the invention relates to a kit of parts according to embodiment 24) or 25) further comprising instructions for the simultaneous, sequential or separate administration of the pharmaceutical compositions.

27) A further embodiment of the invention relates to a kit of parts according to any one of embodiments 24) to 26) for use as a medicament.

28) A further embodiment of the invention relates to a kit of parts according to any one of embodiments 24) to 26) for use in the prevention and/or treatment of a disease or disorder listed in any one of embodiments 9) to 15).

29) A further embodiment of the invention relates to the use of (R)-5-[3-chloro-4-(2,3-dihydroxy-propoxy)-benz[Z]ylidene]-2-([Z]-propylimino)-3-o-tolyl-thiazolidin-4-one and a second active ingredient which is selected from the group consisting of methyl fumarate, dimethyl fumarate, (N,N-diethylcarbamoyl)methyl methyl (2E)but-2-ene-1,4-dioate, and 2-(2,5-dioxopyrrolidin-1-yl)ethyl methyl (2E)but-2-ene-1,4-dioate, or a pharmaceutically acceptable salt thereof, for the manufacture of a medicament for use in the prevention and/or treatment of a disease or disorder listed in any one of embodiments 9) to 15).

30) A further embodiment of the invention relates to the use according to embodiment 29), wherein the second active ingredient is dimethyl fumarate.

31) A further embodiment of the invention relates to the use of (R)-5-[3-chloro-4-(2,3-dihydroxy-propoxy)-benz[Z]ylidene]-2-([Z]-propylimino)-3-o-tolyl-thiazolidin-4-one for the manufacture of a medicament for use, in combination with a second medicament comprising methyl fumarate, dimethyl fumarate, (N,N-diethylcarbamoyl)methyl methyl (2E)but-2-ene-1,4-dioate, or 2-(2,5-dioxopyrrolidin-1-yl) ethyl methyl (2E)but-2-ene-1,4-dioate, or a pharmaceutically acceptable salt thereof, in the prevention and/or treatment of a disease or disorder listed in any one of embodiments 9) to 15).

32) A further embodiment of the invention relates to the use according to embodiment 31), wherein the second medicament comprises dimethyl fumarate.

33) A further embodiment of the invention relates to the use of methyl fumarate, dimethyl fumarate, (N,N-diethylcarbamoyl)methyl methyl (2E)but-2-ene-1,4-dioate, or 2-(2, 5-dioxopyrrolidin-1-yl)ethyl methyl (2E)but-2-ene-1,4-dioate, or a pharmaceutically acceptable salt thereof, for the manufacture of a medicament for use, in combination with a second medicament comprising (R)-5-[3-chloro-4-(2,3-dihydroxy-propoxy)-benz[Z]ylidene]-2-([Z]-propylimino)-3-o-tolyl-thiazolidin-4-one, in the prevention and/or treatment of a disease or disorder listed in any one of embodiments 9) to 15).

34) A further embodiment of the invention relates to the use of dimethyl fumarate for the manufacture of a medicament for use, in combination with a second medicament comprising (R)-5-[3-chloro-4-(2,3-dihydroxy-propoxy)-benz[Z]ylidene]-2-([Z]-propylimino)-3-o-tolyl-thiazolidin-4-one, in the prevention and/or treatment of a disease or disorder listed in any one of embodiments 9) to 15).

Based on the dependencies of the different embodiments 1) to 34) as disclosed hereinabove, the following embodiments are thus possible and intended and herewith specifically disclosed in individualised form: 1, 2+1, 3+1, 4+1, 5+1, 6+1, 6+2+1, 6+3+1, 6+4+1, 6+5+1, 7+1, 7+2+1, 7+3+1, 7+4+1, 7+5+1, 8+1, 8+2+1, 8+3+1, 8+4+1, 8+5+1, 8+6+1, 8+6+2+1, 8+6+3+1, 8+6+4+1, 8+6+5+1, 8+7+1, 8+7+2+1, 8+7+3+1, 8+7+4+1, 8+7+5+1, 9+1, 9+2+1, 9+3+1, 9+4+1, 9+5+1, 9+6+1, 9+6+2+1, 9+6+3+1, 9+6+4+1, 9+6+5+1, 9+7+1, 9+7+2+1, 9+7+3+1, 9+7+4+1, 9+7+5+1, 10+1, 10+2+1, 10+3+1, 10+4+1, 10+5+1, 10+6+1, 10+6+2+1, 10+6+3+1, 10+6+4+1, 10+6+5+1, 10+7+1, 10+7+2+1, 10+7+3+1, 10+7+4+1, 10+7+5+1, 11+1, 11+2+1, 11+3+1, 11+4+1, 11+5+1, 11+6+1, 11+6+2+1, 11+6+3+1, 11+6+4+1, 11+6+5+1, 11+7+1, 11+7+2+1, 11+7+3+1, 11+7+4+1, 11+7+5+1, 12+1, 12+2+1, 12+3+1, 12+4+1, 12+5+1, 12+6+1, 12+6+2+1, 12+6+3+1, 12+6+4+1, 12+6+5+1, 12+7+1, 12+7+2+1, 12+7+3+1, 12+7+4+1, 12+7+5+1, 13+1, 13+2+1, 13+3+1, 13+4+1, 13+5+1, 13+6+1, 13+6+2+1, 13+6+3+1, 13+6+4+1, 13+6+5+1, 13+7+1, 13+7+2+1, 13+7+3+1, 13+7+4+1, 13+7+5+1, 14+1, 14+2+1, 14+3+1, 14+4+1, 14+5+1, 14+6+1, 14+6+2+1, 14+6+3+1, 14+6+4+1, 14+6+5+1, 14+7+1, 14+7+2+1, 14+7+3+1, 14+7+4+1, 14+7+5+1, 15+1, 15+2+1, 15+3+1, 15+4+1, 15+5+1, 15+6+1, 15+6+2+1, 15+6+3+1, 15+6+4+1, 15+6+5+1, 15+7+1, 15+7+2+1, 15+7+3+1, 15+7+4+1, 15+7+5+1, 16, 17, 18+16, 18+17, 19+16, 19+17, 20, 21, 22+20, 22+21, 23+20, 23+21, 24, 25+24, 26+24, 26+25+24, 27+24, 27+25+24, 27+26+24, 27+26+25+24, 28+24, 28+25+24, 28+26+24, 28+26+25+ 24, 29, 30+29, 31, 32+31, 33, and 34.

In the list above the numbers refer to the embodiments according to their numbering provided hereinabove whereas "+" indicates the dependency from another embodiment. The different individualised embodiments are separated by commas. In other words, "6+4+1" for example refers to embodiment 6) depending on embodiment 4), depending on embodiment 1), i.e. embodiment "6+4+1" corresponds to the pharmaceutical combination of embodiment 1) further limited by the features of the embodiments 4) and 6).

Definitions provided herein are intended to apply uniformly to the subject matter as defined in any one of embodiments 1) to 34), and, mutatis mutandis, throughout the description and the claims unless an otherwise expressly set out definition provides a broader or narrower definition. It is well understood that a definition or preferred definition of a term or expression defines and may replace the respective term or expression independently of (and in combination with) any definition or preferred definition of any or all other terms or expressions as defined herein.

Any reference to an active ingredient as defined in any one of embodiments 1) to 34) is to be understood as referring also to the pharmaceutically acceptable salts of such active ingredient, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

The term "pharmaceutical combination", as used herein, refers to a combination of two or more, preferably two, active ingredients, wherein the active ingredients are comprised in a single pharmaceutical composition or in separated pharmaceutical compositions.

The term "active ingredient", as used herein, refers to the pharmaceutically active component of a pharmaceutical composition. Examples of active ingredients, as used herein, are in a first group (R)-5-[3-chloro-4-(2,3-dihydroxy-propoxy)-benz[Z]ylidene]-2-([Z]-propylimino)-3-o-tolyl-thiazolidin-4-one (COMPOUND 1) and in a second group methyl fumarate, dimethyl fumarate, (N,N-diethylcarbamoyl)methyl methyl (2E)but-2-ene-1,4-dioate, and 2-(2,5-dioxopyrrolidin-1-yl)ethyl methyl (2E)but-2-ene-1,4-dioate, or a pharmaceutically acceptable salt thereof (preferably dimethyl fumarate).

The term "simultaneous" or "simultaneously", when used in relation to the administration of active ingredients or of pharmaceutical compositions, means that the administration of a first active ingredient (or of a first pharmaceutical composition, respectively) is still ongoing when the administration of a second active ingredient (or of a second pharmaceutical composition, respectively) is started. Especially, the term "simultaneous" or "simultaneously" means that two active ingredients (or two pharmaceutical compositions, respectively) are administered at the same time, i.e. with the same starting and end time, as is for instance the case for the administration of two active ingredients comprised in a single pharmaceutical composition.

The term "sequential" or "sequentially", when used in relation to the administration of active ingredients or of pharmaceutical compositions, means that the administration of a second active ingredient (or of a second pharmaceutical composition, respectively) is started less than one hour after the administration of a first active ingredient (or of a first pharmaceutical composition, respectively) has been finalized.

The term "separate" or "separately", when used in relation to the administration of active ingredients or of pharmaceutical compositions, means that the administration of a second active ingredient (or of a second pharmaceutical composition, respectively) is started one hour or more (and up to about twelve hours, up to about 24 hours, or up to about 7 days) after the administration of a first active ingredient (or of a first pharmaceutical composition, respectively) has been finalized.

The expressions "to be administered in combination" or "for use, in combination" mean simultaneous, sequential or separate, preferably sequential, administration of active ingredients or pharmaceutical compositions.

The term "route of administration", as used herein, refers to the path by which an active ingredient (e.g. in form of a pharmaceutical composition in a particular dosage form) enters the body. The active ingredients may be administered by enteral (especially oral) or parenteral administration (including topical application or inhalation). Examples of dosage forms which may be used for the administration of the active ingredients are tablets, capsules, pills, powders, solutions, suspensions, emulsions, injectable aqueous or oily solutions or suspensions, suppositories, creams, gels, ear or eye drops, nasal spray, skin patches, or aerosols. Dosage forms for oral administration, such as tablets, capsules, pills, solutions or suspensions are preferred. In case the two active ingredients are comprised in separated pharmaceutical compositions, said separated pharmaceutical compositions may be administered by the same or different routes of administration using the same or different dosage forms.

For the sake of clarity, relapsing multiple sclerosis means relapsing forms of multiple sclerosis which includes forms of multiple sclerosis with relapses. Examples of relapsing multiple sclerosis are relapsing-remitting multiple sclerosis, secondary progressive multiple sclerosis with relapses, and progressive relapsing multiple sclerosis.

The production of pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing COMPOUND 1 and/or a fumarate derivative which is selected from the group consisting of methyl fumarate, dimethyl fumarate, (N,N-diethylcarbamoyl)methyl methyl (2E)but-2-ene-1,4-dioate, and 2-(2,5-dioxopyrrolidin-1-yl)ethyl methyl (2E)but-2-ene-1,4-dioate, or a pharmaceutically acceptable salt thereof, optionally in combination with other therapeutically valuable substances, into a galenical administration form together with suitable, non-toxic, inert, therapeutically compatible solid or liquid carrier materials and, if desired, usual pharmaceutical adjuvants. Formulations for dimethyl fumarate are described in e.g. WO 00/030622 and WO 2010/079222.

The optimal dosing regimen (i.e., the magnitude of the dose and the dosing frequency) for each of the two active ingredients of the pharmaceutical combination according to the present invention may vary depending upon the route of administration, the dosage form, the disease or disorder to be treated, and the particular second active ingredient (fumarate derivative) applied. Further, the dose and/or the dosing frequency may be different during the initial phase and the later phase of the treatment for the first and/or the second active ingredient of the pharmaceutical combination. A preferred dosing regimen for COMPOUND 1 has been disclosed in WO 2009/115954. A preferred maintenance dose for COMPOUND 1 is 10 mg or 20 mg orally once daily, such as especially 20 mg orally once daily. A preferred dosing regimen for dimethyl fumarate is disclosed in WO 2008/097596 (see also U.S. Pat. No. 8,399,514). Most preferably dimethyl fumarate is administered at a starting dose of 120 mg twice a day, orally, for 7 days and a maintenance dose after 7 days of 240 mg twice a day, orally, especially in case of an immediate release formulation such as the one used for Tecfidera®. A preferred dosing regimen for a controlled release pharmaceutical composition of monomethyl fumarate or dimethyl fumarate is disclosed in EP 2316430. A preferred dose for XP23829 is 800 mg orally once daily or 400 mg orally twice daily. A preferred dose for ALKS 8700 is 420 mg orally twice daily.

The present invention also includes isotopically labelled, especially $^2$H (deuterium) labelled active ingredients, which active ingredients are identical to the active ingredients as defined in embodiment 1) except that one or more atoms have each been replaced by an atom having the same atomic number but an atomic mass different from the atomic mass usually found in nature. Isotopically labelled, especially $^2$H (deuterium) labelled active ingredients and pharmaceutically acceptable salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment only one of the two active ingredients of the pharmaceutical combination is isotopically labelled. In a preferred embodiment of the invention, the active ingredients are not isotopically labelled, or one active ingredient is not isotopically labelled and the other active ingredient is labelled only with one or more deuterium atoms, or both active ingredients are each labelled only with one or more deuterium atoms. In a most preferred embodiment, the active ingredients are not isotopically labelled at all. Isotopically labelled active ingredients may be prepared in analogy to the methods described for the not isotopically labelled active ingredients, but using the appropriate isotopic variation of suitable reagents or starting materials.

The term "about" placed before a numerical value "X" refers in the current application to an interval extending from X minus 10% of X to X plus 10% of X.

Biological Assay:

The efficacy of dimethyl fumarate (DMF) in acute monophasic models of experimental autoimmune encephalomyelitis (EAE) can be determined in a pilot experiment.

Female Lewis rats are immunized with an emulsion of myelin basic protein (MBP) from Guinea pig in complete Freund's adjuvant. A total of 200 micrograms of MBP is injected per rat at two sites subcutaneously (right paw and base of tail). Within 10 days the rats develop signs of paralysis which will be graded on a scale from 0 to 15 assessing the tail and each limb individually according to the method originally described by Weaver A. et al., *FASEB J.*, 2005, 19(12): 1668-1670. The disease takes an acute monophasic course and is self-remitting. Usually by day 21 clinical scores reach values below 3.0.

Groups of 10 to 14 rats are dosed starting at the day of disease induction (day 0) with different doses of DMF in the range between 40 and 160 mg/kg once daily (q.d.). Clinical scores are assessed on a daily basis and disease development is compared between vehicle-treated rats and rats receiving DMF (vehicle: 0.5% Methylcellulose/0.5% Tween® 80). In parallel, body weights of the rats are monitored on a daily basis to follow general health. The experiment is terminated at day 21 whereupon hematology can be measured.

Plasma samples can be taken for compound concentration determination and for the measurement of protein markers. Different organs may be isolated and fixed for histopathological examination, particularly the spinal cord and the brain. Spinal cord tissue preparations can be used to assess the degree of demyelination, neuronal loss and inflammatory cell infiltration by different staining methods (H&E, Luxol Fast Blue for myelin, MBP, NeuN, CD3, Nrf2 and other markers by immunohistochemistry for demyelination, neuronal loss, T cell infiltration, antioxidant pathway activation and other pathways, respectively). Additional tissue samples may be preserved in RNAlater® solution for analysis of gene expression.

In parallel to the measurement of efficacy of DMF in the EAE model, a second pilot experiment is required. Healthy female Lewis rats will receive ponesimod at different doses in the range from 0.3 to 100 mg/kg. The goal is to assess the dose-effect relationship of ponesimod on lymphocyte count in peripheral blood in this strain of rat.

Based on the first pilot experiment described above one dose of DMF is selected for the combination efficacy experiment. The dose selected exerts partial efficacy between none and strongest efficacy on EAE scores (dose 120 mg/kg).

Based on the second pilot experiment using ponesimod, the dose selected shows full efficacy on lymphocyte count reduction (dose 100 mg/kg).

The combination efficacy experiment is performed in the same rat EAE model as described for the first pilot experiment. It consists of four treatment groups:
1. Vehicle (0.5% Methylcellulose/0.5% Tween® 80) q.d., from day 0
2. DMF (120 mg/kg) q.d., from day 0
3. Ponesimod (100 mg/kg) q.d., from day 0
4. DMF (120 mg/kg) q.d., from day 0+ponesimod (100 mg/kg) q.d., from day 0

In life and termination endpoints are the same as described for the first pilot experiment.

The goal of this experiment is to show that the addition of a dose of ponesimod, that is fully efficacious on lymphocyte count, shows added benefit to a partially efficacious dose of DMF in a model of EAE.

The results from the combination efficacy experiment are shown in FIG. 1. As can be seen from FIG. 1, both compounds, ponesimod and DMF exhibit efficacy on the clinical course of EAE in the rat monophasic EAE model. Ponesimod showed a marked and statistically significant effect while DMF alone showed a moderate effect during the ascending phase of the disease. When combined, the two compounds showed synergistic efficacy from day 16 onwards, where DMF alone had no effect on clinical score anymore.

The invention claimed is:
1. A method of treating multiple sclerosis comprising the steps of administering a synergistically effective amount of:
(R)-5-[3-chloro-4-(2,3-dihydroxy-propoxy)-benz[Z]ylidene]-2-([Z]-propylimino)-3-o-tolyl-thiazolidin-4-one (Compound 1) or a pharmaceutically acceptable salt thereof to a patient in need thereof; and b) dimethyl fumarate to the patient,
wherein the dimethyl fumarate is administered simultaneously, sequentially or separately from Compound 1 or a pharmaceutically acceptable salt thereof to the patient.

2. The method according to claim 1, wherein the multiple sclerosis is relapsing multiple sclerosis.

3. The method according to claim 1, wherein the multiple sclerosis is relapsing-remitting multiple sclerosis.

4. The method according to claim 1, wherein the dimethyl fumarate is administered simultaneously with Compound 1 or a pharmaceutically acceptable salt thereof.

5. The method according to claim 1, wherein the dimethyl fumarate is administered sequentially with Compound 1 or a pharmaceutically acceptable salt thereof.

6. The method according to claim 1, wherein the dimethyl fumarate is administered separately from Compound 1 or a pharmaceutically acceptable salt thereof.

7. The method according to claim 1, wherein Compound 1 or a pharmaceutically acceptable salt thereof is administered once daily, and the dimethyl fumarate is administered twice daily to the patient.

8. The method according to claim 1, wherein Compound 1 or a pharmaceutically acceptable salt thereof is administered orally; and/or dimethyl fumarate is administered orally.

9. A pharmaceutical combination comprising:
about 10 or about 20 mg of (R)-513-chloro-4-(2,3-dihydroxy-propoxy)-benz[Z]ylidene]-2-([4-propylimino)-3-o-tolyl-thiazolidin-4-one (Compound 1) or a pharmaceutically acceptable salt thereof; and
dimethyl fumarate,
wherein the(R)-513-chloro-4-(2,3-dihydroxy-propoxy)-benz[Z]ylidene]-2-([Z]-propylimino)-3-o-tolyl-thiazolidin-4-one and the dimethyl fumarate are in synergistically effective amounts for the treatment of multiple sclerosis.

10. The pharmaceutical combination of claim 9, comprising about 120 mg of dimethyl fumarate.

11. The pharmaceutical combination of claim 9, comprising about 240 mg of dimethyl fumarate.

12. The pharmaceutical combination of claim 9, comprising about 10 mg of Compound 1 or a pharmaceutically acceptable salt thereof.

13. The pharmaceutical combination of claim 9, comprising about 20 mg of Compound 1 or a pharmaceutically acceptable salt thereof.

14. The pharmaceutical combination of claim 9, wherein Compound 1 or a pharmaceutically acceptable salt thereof and dimethyl fumarate are comprised in a single pharmaceutical composition.

15. The pharmaceutical combination of claim 9, wherein Compound 1 or a pharmaceutically acceptable salt thereof and dimethyl fumarate are comprised in separate pharmaceutical compositions.

* * * * *

UNITED STATES PATENT AND TRADEMARK OFFICE
CERTIFICATE OF CORRECTION

PATENT NO. : 11,672,783 B2
APPLICATION NO. : 17/325912
DATED : June 13, 2023
INVENTOR(S) : Martine Clozel et al.

It is certified that error appears in the above-identified patent and that said Letters Patent is hereby corrected as shown below:

On the Title Page

Item (57) In Abstract, Under Column No. 2, Line nos. 3-4, Replace:
"2-([Z]propylimino)-"
With:
--2-([Z]-propylimino)- --

In the Claims

Under Column No. 10, in Claim 1, Line no. 64, Replace:
"(R)-5-"
With:
--a) (R)-5- --

Under Column No. 11, in Claim 9, Line no. 27, Replace:
"(R)-513-chloro-"
With:
--(R)-5-[3-chloro- --

Under Column No. 11, in Claim 9, Line no. 28, Replace:
"([4-propylimino)-"
With:
--([Z]-propylimino)- --

Under Column No. 12, in Claim 9, Line no. 4, Replace:
"the(R)-513-chloro"
With:
--the (R)-5-[3-chloro--

Signed and Sealed this
Twenty-ninth Day of August, 2023

*Katherine Kelly Vidal*
Katherine Kelly Vidal
*Director of the United States Patent and Trademark Office*